United States Patent
Shirata (10) Patent No.: US 10,359,401 B2
(45) Date of Patent: Jul. 23, 2019

(54) MALFUNCTION DIAGNOSING APPARATUS, MALFUNCTION DIAGNOSING METHOD, AND RECORDING MEDIUM

(71) Applicant: Yasunobu Shirata, Tokyo (JP)

(72) Inventor: Yasunobu Shirata, Tokyo (JP)

(73) Assignee: RICOH COMPANY, LTD., Tokyo (JP)

(*) Notice: Subject to any disclaimer, the term of this patent is extended or adjusted under 35 U.S.C. 154(b) by 7 days.

(21) Appl. No.: 15/397,080

(22) Filed: Jan. 3, 2017

(65) Prior Publication Data
US 2017/0199164 A1 Jul. 13, 2017

(30) Foreign Application Priority Data

Jan. 7, 2016 (JP) .................................. 2016-002097
Oct. 25, 2016 (JP) .................................. 2016-208970

(51) Int. Cl.
*G01N 29/46* (2006.01)
*B41J 2/045* (2006.01)
(Continued)

(52) U.S. Cl.
CPC ............ *G01N 29/46* (2013.01); *B41J 2/0451* (2013.01); *B41J 2/04586* (2013.01);
(Continued)

(58) Field of Classification Search
None
See application file for complete search history.

(56) References Cited

U.S. PATENT DOCUMENTS

2005/0262394 A1   11/2005   Yasukawa et al.
2007/0033153 A1*  2/2007   Yamanaka ............. G01V 1/008
                                                706/21
(Continued)

FOREIGN PATENT DOCUMENTS

EP   2596952 A1      5/2013
EP   3189969    *  12/2017  ............ B41J 29/293
(Continued)

OTHER PUBLICATIONS

Office Action for European Patent Application No. 16206764.9 dated May 3, 2019.

*Primary Examiner* — Tung S Lau
(74) *Attorney, Agent, or Firm* — Harness, Dickey & Pierce, P.L.C.

(57) ABSTRACT

A malfunction diagnosing apparatus includes circuitry that collects vibration data generated when a diagnosed apparatus operates in a predetermined operating sequence, analyzes the collected vibration data and calculate a feature quantity, determines, based on the calculated feature quantity, whether or not something is wrong with the diagnosed apparatus, controls, if it is determined that something wrong with the diagnosed apparatus, the diagnosed apparatus to repeat the operating sequence that it is determined that something is wrong with the diagnosed apparatus for a predetermined number of times, and determines that malfunction occurs in the diagnosed apparatus if it is determined that something is wrong with the diagnosed apparatus in the operating sequence repeated for the predetermined number of times.

13 Claims, 10 Drawing Sheets

(51) Int. Cl.
  *B41J 29/393* (2006.01)
  *G01N 29/14* (2006.01)
  *G08B 21/18* (2006.01)

(52) U.S. Cl.
  CPC ............ *B41J 29/393* (2013.01); *G01N 29/14* (2013.01); *G08B 21/187* (2013.01); *G01N 2291/028* (2013.01)

(56) References Cited

U.S. PATENT DOCUMENTS

2010/0060690 A1    3/2010   Hosokawa et al.
2015/0057956 A1*   2/2015   Ooe .................... G01M 13/045
                                                                                                     702/56
2017/0199164 A1*   7/2017   Shirata ................... B41J 29/393

FOREIGN PATENT DOCUMENTS

| JP | H09-229762 A | 9/1997 |
| --- | --- | --- |
| JP | 2007-223750 | 9/2007 |
| JP | 2010-054558 | 3/2010 |
| JP | 2013-109281 | 6/2013 |
| JP | 2014-092504 A | 5/2014 |
| JP | 2015-041337 | 3/2015 |

* cited by examiner

CHARACTERISTIC AMOUNT OF INPUT DATA

FIG. 5B

CHARACTERISTIC AMOUNT OF NORMAL DATA

FIG. 5C

DIFFERENCE IN CHARACTERISTIC AMOUNTS

FIG. 6A
CHARACTERISTIC AMOUNT OF INPUT DATA

FIG. 6B
CHARACTERISTIC AMOUNT OF CANDIDATE FOR MALFUNCTION

FIG. 6C
DIFFERENCE IN CHARACTERISTIC AMOUNTS

| NUMBER | SEQUENCE OF OPERATION | NUMBER OF REPEATS : Nx |
|---|---|---|
| 1 | OPERATION A → OPERATION B → OPERATION C | N1 |
| 2 | OPERATION D → OPERATION E | N2 |
| 3 | OPERATION F | N3 |
| 4 | OPERATION G → OPERATION H → OPERATION I → OPERATION J | N4 |
| 5 | OPERATION K → OPERATION L | N5 |
| .. | .. | .. |
| m | OPERATION ZZ | Nm |

| ALERT LEVEL | COUNTER | DETERMINATION RESULT |
|---|---|---|
| LEVEL 1 | 1 ≤ COUNTER < 3 | NORMAL |
| LEVEL 2 | 3 ≤ COUNTER < 5 | NORMAL |
| LEVEL 3 | 5 ≤ COUNTER | NORMAL |
| LEVEL 4 | ·· | MALFUNCTION |

MALFUNCTION DIAGNOSING APPARATUS, MALFUNCTION DIAGNOSING METHOD, AND RECORDING MEDIUM

CROSS-REFERENCE TO RELATED APPLICATION

This patent application is based on and claims priority pursuant to 35 U.S.C. § 119(a) to Japanese Patent Applications No. 2016-002097, filed on Jan. 7, 2016 and No. 2016-208970, filed on Oct. 25, 2016 in the Japan Patent Office, the entire disclosure of which is hereby incorporated by reference herein.

BACKGROUND

Technical Field

The present invention relates to a malfunction diagnosing apparatus, a malfunction diagnosing method, and a non-transitory recording medium storing a malfunction diagnosing program.

Background Art

In malfunction diagnosing systems that detect malfunction of apparatuses, a technology that samples sound generated inside the apparatuses into vibration data, and detects malfunction of apparatuses based on acquired vibration data is known.

In existing methods that detect malfunction of apparatuses using sound data, malfunction of the target apparatus is determined based on a one-time detection result. Therefore, the target apparatus is easily determined as abnormal, even based on a sound that is accidentally generated at the time of diagnosing malfunction, thus leading to an error in diagnosing.

SUMMARY

Example embodiments of the present invention provide a novel malfunction diagnosing apparatus that includes circuitry that collects vibration data generated when a diagnosed apparatus operates in a predetermined operating sequence, analyzes the collected vibration data and calculate a feature quantity, determines, based on the calculated feature quantity, whether or not something is wrong with the diagnosed apparatus, controls, if it is determined that something wrong with the diagnosed apparatus, the diagnosed apparatus to repeat the operating sequence that it is determined that something is wrong with the diagnosed apparatus for a predetermined number of times, and determines that malfunction occurs in the diagnosed apparatus if it is determined that something is wrong with the diagnosed apparatus in the operating sequence repeated for the predetermined number of times.

Further example embodiments of the present invention provide a method of diagnosing malfunction and a non-transitory recording medium storing a malfunction diagnosing program.

BRIEF DESCRIPTION OF THE DRAWINGS

A more complete appreciation of the disclosure and many of the attendant advantages thereof will be readily obtained as the same becomes better understood by reference to the following detailed description when considered in conjunction with the accompanying drawings.

The accompanying drawings are intended to depict example embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing preferred embodiments illustrated in the drawings, specific terminology is employed for the sake of clarity. However, the disclosure of this patent specification is not intended to be limited to the specific terminology so selected, and it is to be understood that each specific element includes all technical equivalents that have the same function, operate in a similar manner, and achieve a similar result.

A more complete appreciation of the disclosure and many of the attendant advantages thereof will be readily obtained as the same becomes better understood by reference to the following detailed description when considered in conjunction with the accompanying drawings.

Embodiments of the present invention are described below in detail with reference to figures. In figures, same symbols are assigned to same or corresponding parts, and their descriptions are simplified or omitted appropriately.

Figure 1:
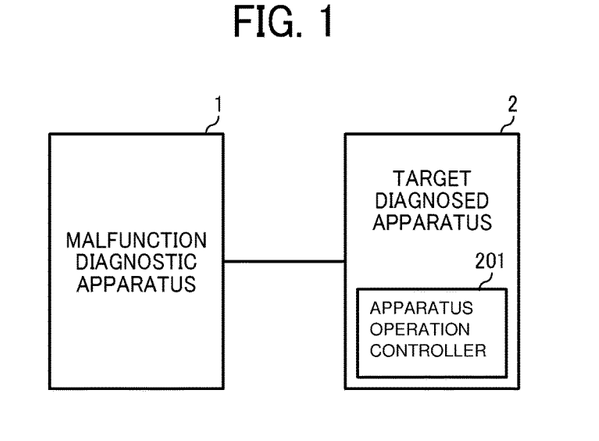
FIG. 1 is a diagram illustrating an entire configuration of a system including a malfunction diagnosing apparatus as an embodiment of the present invention.

FIG. 1 is a diagram illustrating an entire configuration of a system including a malfunction diagnosing apparatus in this embodiment.

As illustrated in FIG. 1, a malfunction diagnosing apparatus 1 collects information generated when a diagnosed apparatus 2 as a diagnosing target operates in a predetermined operating sequence, and determines whether or not the diagnosed apparatus 2 operates abnormally based on the collected information.

The malfunction diagnosing apparatus 1 may be connected to the diagnosed apparatus 2 in many ways. For example, the diagnosed apparatus 2 may be connected to a diagnosing apparatus 100 using a dedicated connection line, a wired network such as a wired local area network (LAN), and a wireless network etc.

Figure 2:
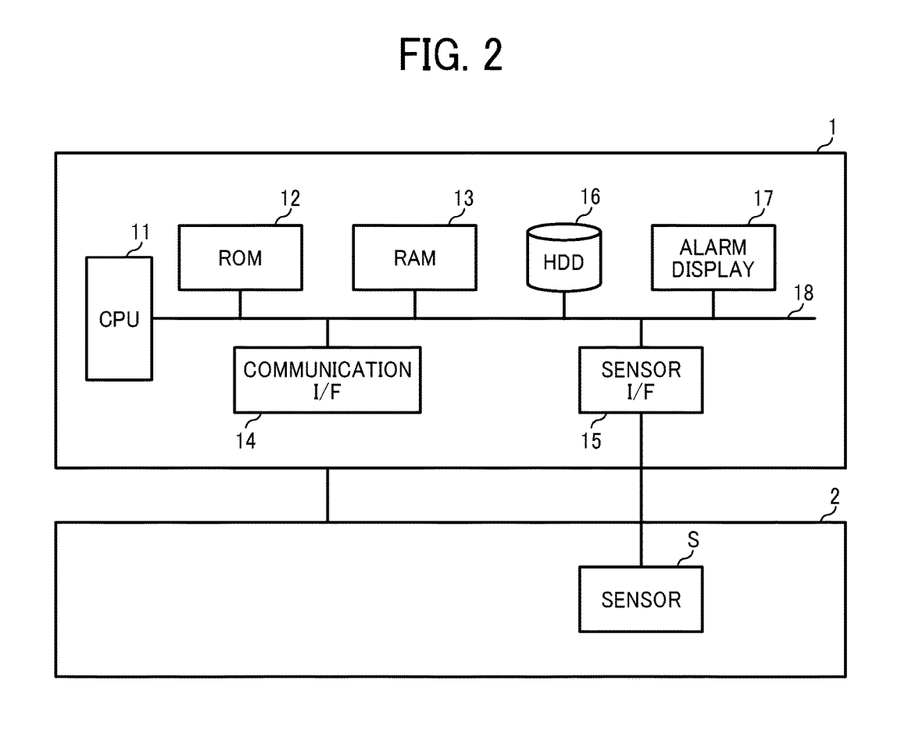
FIG. 2 is a diagram illustrating a hardware configuration of the malfunction diagnosing apparatus in FIG. 1 as an embodiment of the present invention.

FIG. 2 is a diagram illustrating a hardware configuration of the malfunction diagnosing apparatus 1 in FIG. 1 in this embodiment.

As illustrated in FIG. 2, the malfunction diagnosing apparatus 1 includes a central processing unit (CPU) 11, a read only memory (ROM) 12, a random access memory (RAM) 13, a communication interface (I/F) 14, a sensor I/F 15, a hard disk drive (HDD) 16, and an alarm display 17, and those components are connected with each other via a bus 18.

The CPU 11 controls the entire malfunction diagnosing apparatus 1. For example, the CPU 11 controls the entire malfunction diagnosing apparatus 1 to implement a diagnosing function by executing a program stored in the ROM 12 etc. using the RAM 13 as a work area. The communication I/F 14 is an interface for communicating with the diagnosed apparatus 2. The malfunction diagnosing apparatus 1 communicates with the diagnosed apparatus 2 via the communication I/F 14, and the malfunction diagnosing apparatus 1 transfers an operating sequence (described later) and the number of times executing the operating sequence etc. to the diagnosed apparatus 2 to perform the operating sequence. The sensor I/F 15 converts analog signals acquired by a sensor S (described later) located inside the diagnosed apparatus 2 to digital signals. The HDD 16 stores configuration information of the malfunction diagnosing apparatus 1 and detected information received from the sensor S etc. The alarm display 17 displays information when the malfunction diagnosing apparatus 1 detects malfunction of the diagnosed apparatus 2 and reports to an external apparatus about the malfunction of the diagnosed apparatus 2.

Figure 3:
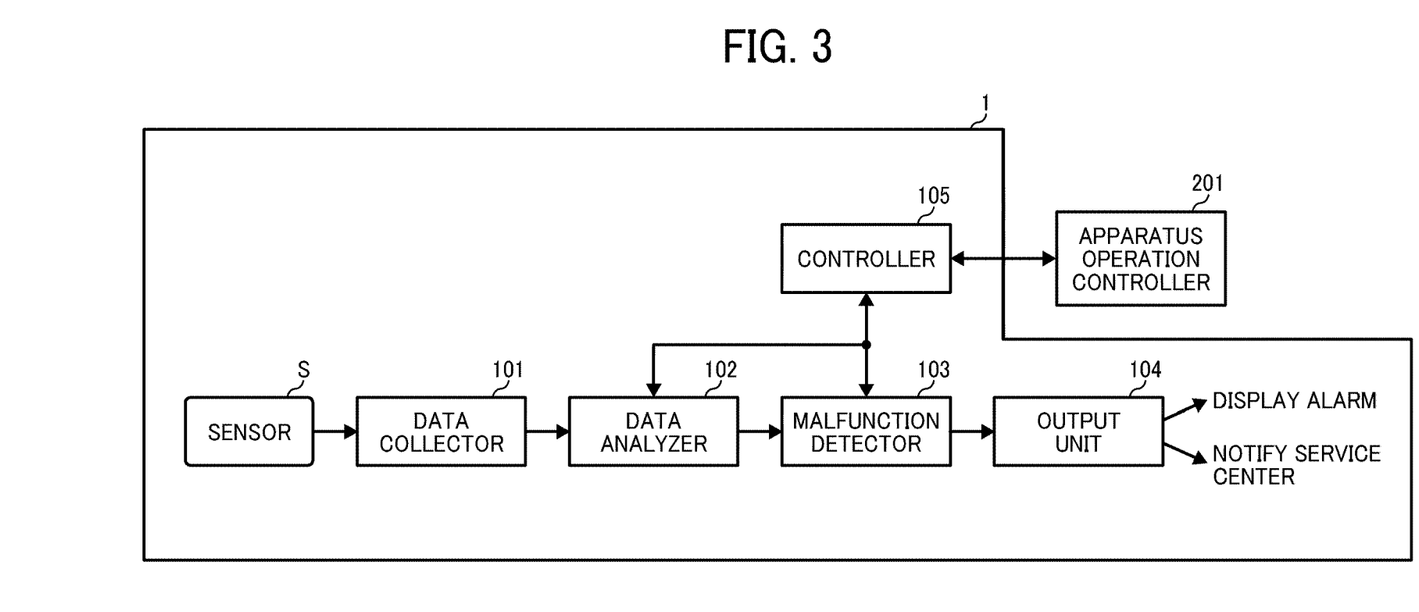
FIG. 3 is a diagram illustrating functional blocks of the malfunction diagnosing apparatus as an embodiment of the present invention.

FIG. 3 is a diagram illustrating functional blocks of the malfunction diagnosing apparatus 1 in this embodiment.

As illustrated in FIG. 3, the malfunction diagnosing apparatus 1 includes a data collector 101, a data analyzer 102, a malfunction detector 103, an output unit 104, and a controller 105. Those functional units, the data collector 101, the data analyzer 102, the malfunction detector 103, the output unit 104, and the controller 105, are implemented by executing a program stored in the ROM 12 by the CPU 11 and controlling the communication I/F 14, the sensor I/F 15, and the HDD 16.

The data collector 101 amplifies a weak electric signal received from the sensor S to convert it into an analog electric signal in a predetermined voltage level (several hundred millivolts) and outputs the analog electric signal to the data analyzer 102.

For example, the sensor S may include a microphone that captures sound, a vibration sensor that captures vibration, and an acoustic emission (AE) sensor that captures an elastic wave. The AE sensor detects acoustic emission generated when deformation and destruction locally occurs in a material. Target for sensing by the sensor S may be sound, vibration, and acoustic emission (hereinafter collectively referred to as "vibration data") and those are generated when a motor drives to operate a unit inside the apparatus to be diagnosed, a bearing rotates, or a cutting operation is performed by a machine tool.

The data analyzer 102 converts the electric signal (low frequency analog signal) input from the data collector 101 into a digital signal, and analyzes the digital signal to calculate a feature quantity of the input data.

For example, fast Fourier transform (FFT) is used to calculate the feature quantity. In Fourier transform, components for each frequency (sound pressure level) is calculated from the digital signal, which is generally referred to as spectrum analysis. After performing spectrum analysis, the analyzed data is output to the malfunction detector 103.

Based on the feature quantity calculated by the data analyzer 102, the malfunction detector 103 determines whether or not the feature quantity reflects abnormality and inputs the determination result to the output unit 104.

The output unit 104 transfers the determination result input from the malfunction detector 103 to the alarm display 17 to request the alarm display 17 to turn on an alarm, notifying that the determination result indicates abnormality, and further send e-mail to a service center in charge of maintenance via the Internet etc.

The controller 105 requests the data analyzer 102 to start calculating the feature quantity, and requests an apparatus operation controller 201 in the diagnosed apparatus 2 to perform the same operation again via the communication I/F 14 based on the determination result of the malfunction detector 103 indicating abnormality. The controller 105 further controls to modify a criterion for determining abnormality by the malfunction detector 103.

Embodiment 1

Next, an operation of determining abnormality of the target apparatus, performed by the malfunction diagnosing apparatus, is described according to an embodiment.

In this embodiment, in operating the diagnosed apparatus in a predetermined sequence, if it is determined that the diagnosed apparatus operates abnormally for the first time, the diagnosed apparatus is instructed to repeat the operating sequence. Subsequently, if it is determined that the diagnosed apparatus operates abnormally again, it is determined that malfunction occurs.

Figure 4:
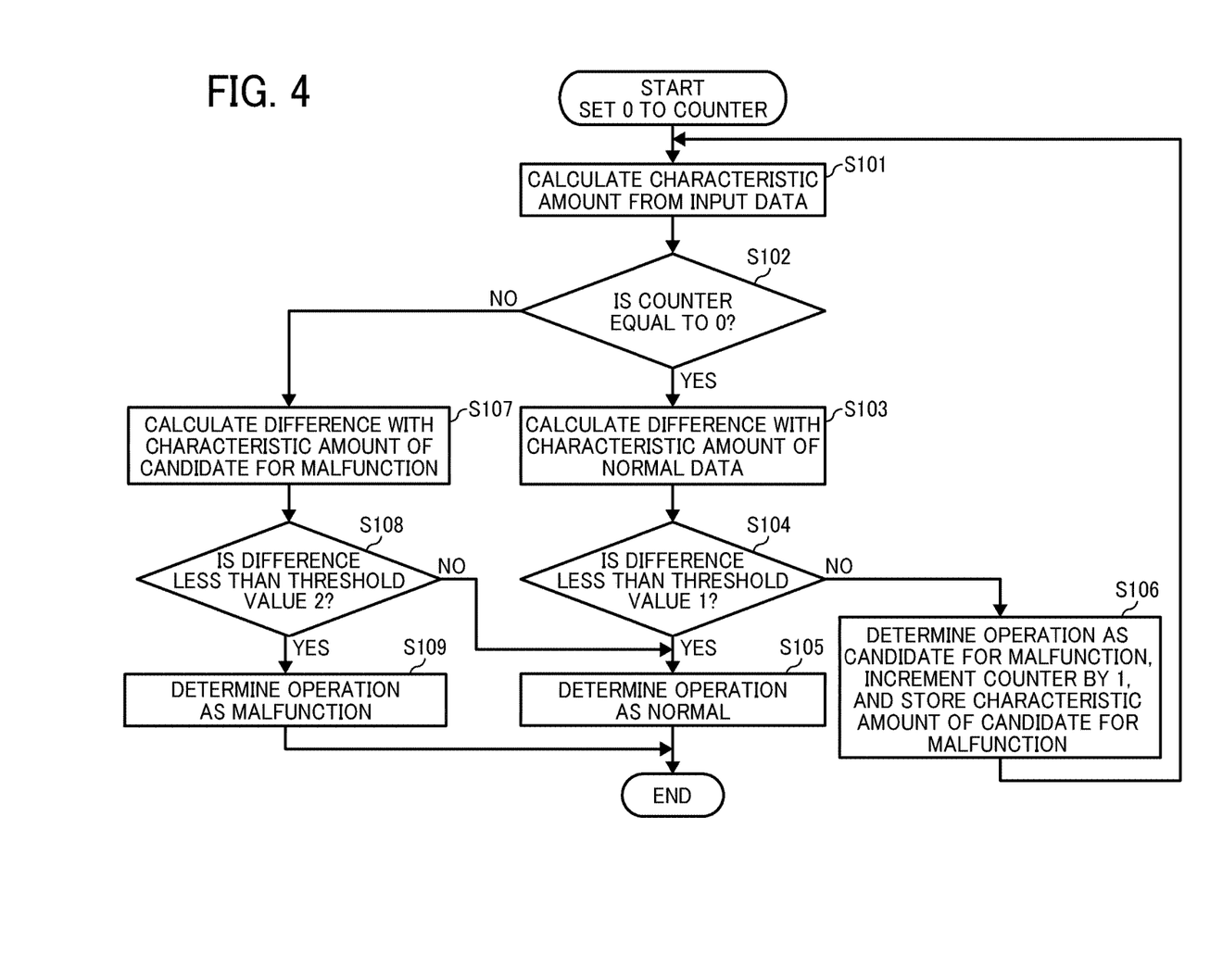
FIG. 4 is a flowchart illustrating an operation of determining malfunction as an embodiment of the present invention.

FIG. 4 is a flowchart illustrating an operation of determining malfunction, performed by the CPU 11 of the malfunction diagnosing apparatus 1, in this embodiment.

In starting to determine whether or not the diagnosed apparatus operates abnormally, a counter variable in a counter value memory that stores a number of determinations is initialized to 0 (that is, a counter value is initialized to 0). Subsequently, the data analyzer 102 calculates the feature amount from the sensor data (input data) input from the data collector 101 in S101. That is, the data analyzer 102 performs the Fourier transform described before for example and calculates sound pressure for each frequency (i.e., spectrum) as the feature quantity.

Next, with reference to the counter value, if the counter value is 0, which indicates that no determination has been performed in the past (YES in S102), the feature quantity of normal data is compared with the feature quantity of the input data, and difference between the feature quantities is calculated in S103. It should be noted that the feature quantity of the normal data is stored in the ROM preliminarily by collecting sensing data when the apparatus operates normally by the controller 105. In this embodiment, for each one of a plurality of operating sequences, the feature quantity for normal data is stored, which reflects the state when the apparatus operates normally. The difference between the feature quantity of the normal data corresponding to the operating sequence of the input data, and the feature quantity of the input data is calculated for each frequency.

Next, it is determined whether or not the difference between the feature quantity of the normal data and the feature quantity of the input data calculated for each frequency is less than a predetermined threshold value 1 in S104. If the difference is less than the threshold 1 (YES in S104), it is determined that the input data is normal in S105, and the operation ends.

By contrast, if it is determined that the difference for each dimension of frequency is equal to or larger than the predetermined threshold value 1 (NO in S104), it is determined that the input data is a candidate of data reflecting malfunction ("malfunction data candidate") in S106, and the operation goes back to S101.

In this case, the malfunction detector 103 increments the counter value by 1 and stores the feature quantity of the input data as the feature quantity of the malfunction data candidate in S106 and reports to the controller 105 that the same operating sequence is to be performed again after finishing a current operating sequence. The controller 105 requests the apparatus operation controller to perform the reported operating sequence.

In S101, the data analyzer 102 calculates again the feature quantity of the input data, which is generated when performing the operating sequence same as the previously-performed operation that indicates malfunction. In this case, since the counter value is incremented by 1 in S105 previously, it is determined that the counter value is not 0 (NO in S102), and the operation proceeds to S107.

In S107, difference between the feature quantity of the malfunction data candidate (i.e., input data input in S101 in the previous operating sequence) stored in the memory in S106 and the feature quantity of the input data is calculated, and the calculated difference is compared with a threshold value 2 in S108.

In this case, if the calculated difference is less than the predetermined threshold value 2 (YES in S108), it is determined that the feature quantity of the input data in S109 is abnormal data. That is, even in the second comparison, it is determined that the feature quantity of the input data is almost the same as the feature quantity of the previously-obtained malfunction data candidate. As a result, it is determined that the abnormal data is obtained, indicating malfunction.

If the calculated difference is equal to or larger than the predetermined threshold value 2 (NO in S108), since the feature quantity of the input data is different from the feature quantity of the abnormal data candidate in the second comparison, it is determined that the data is normal in S105, and the operation ends.

It should be noted that the determination result is passed to the output unit 104.

If the malfunction detector 103 determines a malfunction in S109, the output unit 104 requests the separate alarm display to display alarm so that the alarm is turned on and reports to the remote service center that the diagnosed apparatus operates abnormally.

Figure 5A:
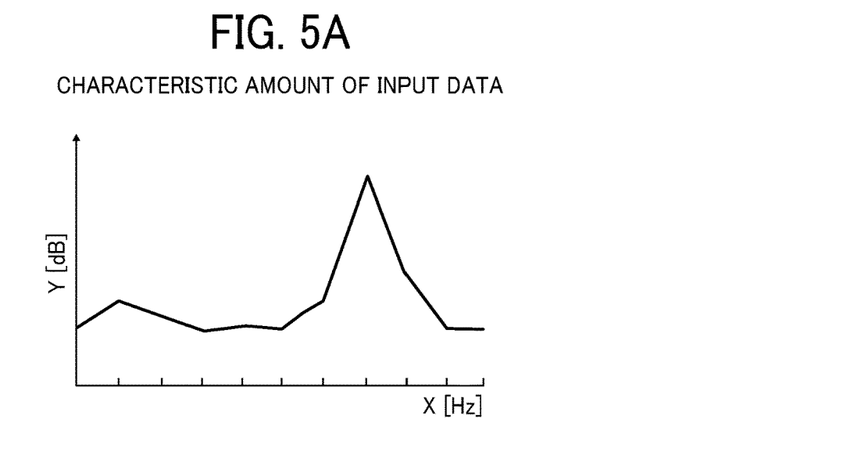
FIGS. 5A, 5B, and 5C are diagrams illustrating a spectrum chart of vibration data (sensing data) of an apparatus detected by a sensor indicating frequency in the X-axis and sound pressure level (dB) in the Y-axis.
Figure 5B:
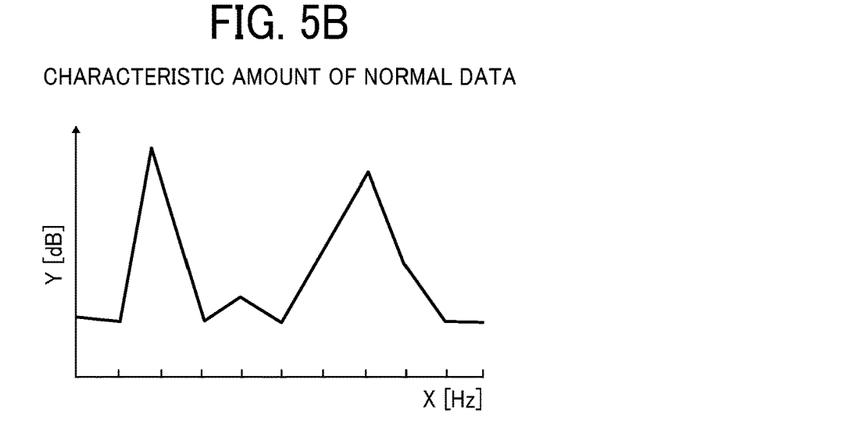
Figure 5C:
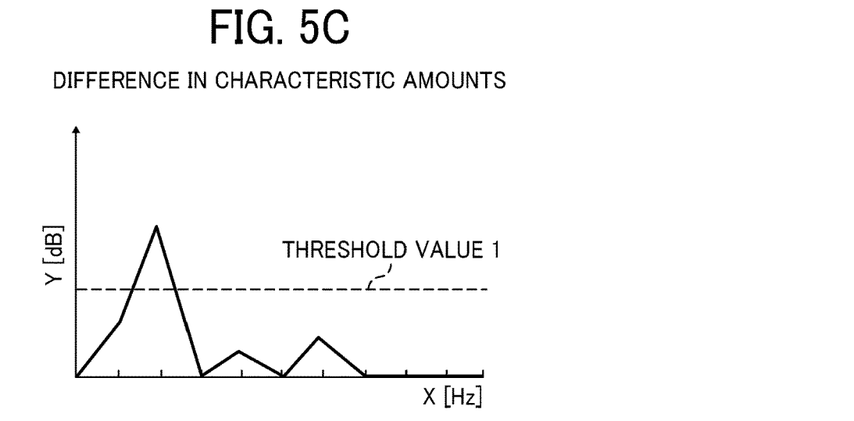

FIGS. 5A, 5B, and 5C are diagrams illustrating a spectrum chart of vibration data (sensing data) of an apparatus detected by a sensor S, showing frequency in the X-axis and sound pressure level (dB) in the Y-axis.

FIG. 5A is a spectrum chart illustrating a feature quantity of sensing data in a current operating sequence.

FIG. 5B is a spectrum chart of normal data. The spectrum chart for normal data is preliminarily stored for each diagnosed apparatus. Regarding spectrum charts for normal data, average values of sound pressure level for each frequency is preliminarily stored using multiple sensing data when the apparatus operates normally.

FIG. 5C is a diagram illustrating difference between the feature quantity of the input sensing data in FIG. 5A and the feature quantity of the normal data in FIG. 5B. The difference indicates the calculated feature quantity of the normal data and the input data in S103 described before, that is, the difference of feature quantity data (dB) for each frequency.

In S104, the difference between the feature quantity of the input data and the feature quantity of the normal data is calculated for each frequency. After comparing the calculated differences with the predetermined threshold value 1 for each frequency, if the calculated difference is less than the threshold value 1, it is determined that the apparatus operates normally. By contrast, if the calculated difference is equal to or larger than the threshold value 1, it is determined that the apparatus operates abnormally.

It should be noted that the threshold value 1 is a predetermined value configured preliminarily and stored in the ROM preliminarily. In the above description, the same operating sequence is performed after finishing performing the sequence determined as generating the candidate for malfunction data in S106. However, the same operating sequence may be performed on another occasion.

For example, in case of performing operating sequences multiple times sequentially, after completing all of the operating sequences, only the sequence determined as generating the candidate for malfunction data may be performed again.

Figure 6A:
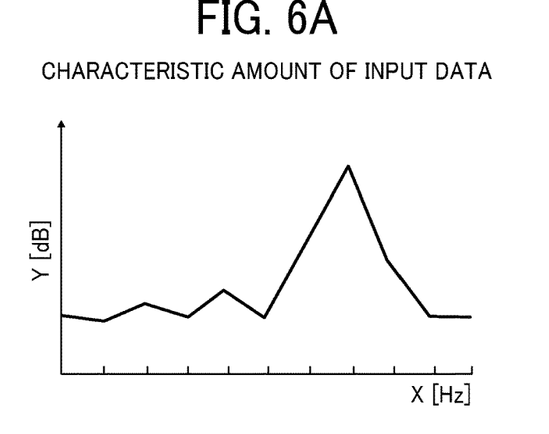
FIGS. 6A, 6B, and 6C are diagrams illustrating differences of feature quantity data for each frequency calculated in S107.
Figure 6B:
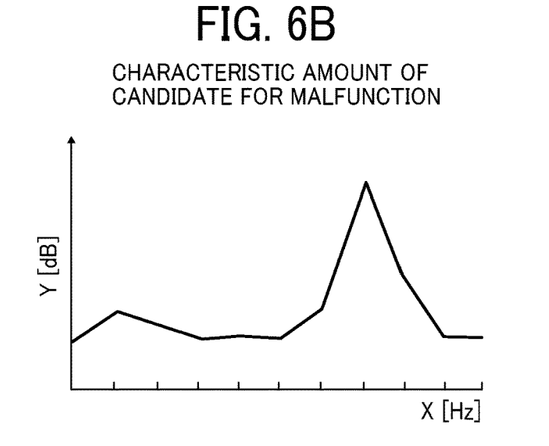
Figure 6C:
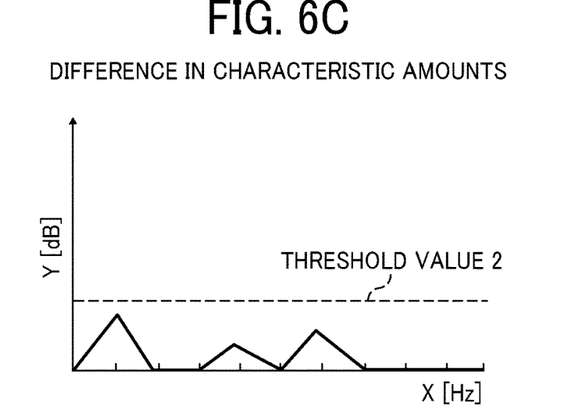

While diagrams illustrated in FIGS. 6A to 6C are similar to diagrams illustrated in FIGS. 5A to 5C, in this case, instead of the feature quantity of the normal data in FIG. 5B, in FIG. 6B, the feature quantity of the malfunction data candidate (i.e., the feature quantity stored in S106 in case the counter value is 0 and it is determined that abnormality occurs in S104) is illustrated. In FIG. 6C, difference between the feature quantity of the input sensing data illustrated in FIG. 6A and the feature quantity of the mulfunction data candidate illustrated in FIG. 6B is illustrated. After calculating the feature quantity of the abnormal data candidate and the input data in S107, the difference described above indicates the difference of the feature quantity data (dB) for each frequency.

In S108, the difference between the feature quantity of the input data and the feature quantity of the malfunction data candidate is calculated for each frequency. After comparing the calculated differences with the predetermined threshold value 2 for each frequency, if the calculated difference is less than the threshold value 2, it is determined that the apparatus operate abnormally. By contrast, if the calculated difference is equal to or larger than the threshold value 2, it is determined that the apparatus operates normally. It should be noted that the threshold value 2 is a predetermined value configured preliminarily and stored in the ROM 12 preliminarily.

Embodiment 2

In this embodiment, after diagnosing the apparatus, if it is determined that the apparatus operates abnormally for the first time, the operating sequence determined as generating the malfunction data is repeated. If it is determined that the apparatus operates abnormally for multiple times consecutively, it concludes that malfunction occurs.

That is, in the first embodiment, in performing the operating sequence indicating a malfunction of the diagnosed apparatus again, and if it is also determined that the diagnosed apparatus operates abnormally in the second time, the diagnosing apparatus 1 determines that the diagnosed apparatus operates abnormally. However, in this embodiment, if it is determined that the diagnosed apparatus operates for a number of times equal to or larger than the predetermined number of repetition times N (i.e., N is equal to or larger than 1), it concludes that malfunction occurs. That is, the following embodiment is substantially the same as the first embodiment described above, except that the number of repetition times N is modifiable.

Figure 7:
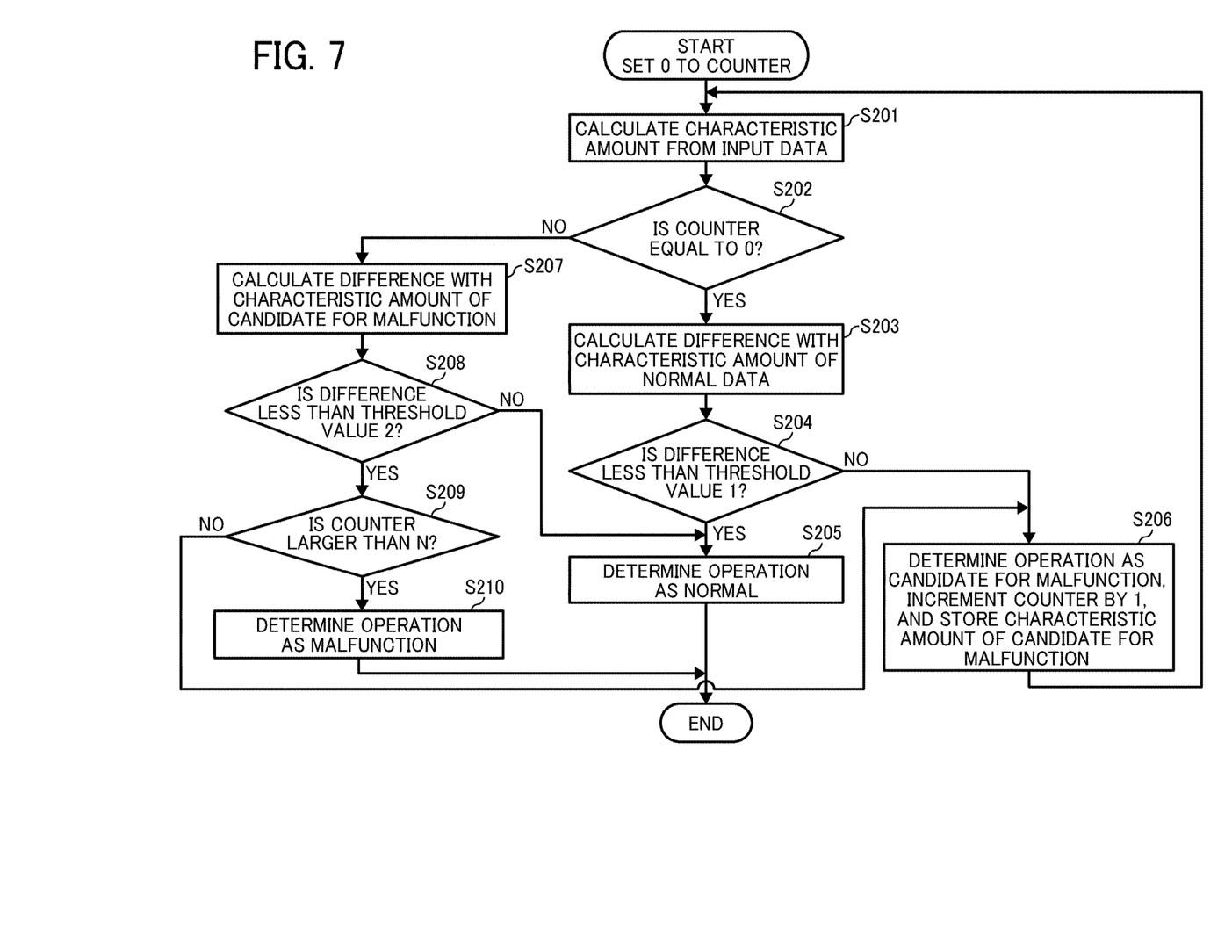
FIG. 7 is a flowchart illustrating an operation of determining malfunction as an embodiment of the present invention.

FIG. 7 is a flowchart illustrating an operation of determining malfunction in this embodiment.

Referring to FIG. 7, in starting to determine whether or not the diagnosed apparatus operates abnormally, a counter variable in a counter value memory that stores the number of determination is initialized to 0.

Here, steps S201 to S207 are substantially the same as steps S101 to S107 in the first embodiment, so the descriptions for those steps are omitted with reference to the description in the first embodiment.

In S208, a difference between the feature quantity of the malfunction data candidate stored in the memory in S206 and the feature quantity of the input data is calculated, and the calculated difference is compared with a threshold value 2. In this case, if the calculated difference is equal to or larger than the threshold value 2 (NO in S208), it is determined that the apparatus operates normally in S205, and the operation ends.

If the calculated difference is less than 2 (YES in S208), it is compared whether or not the counter value is larger than N in S209. Here, N is an integer value that defines the number of times the malfunction data candidate should be obtained to conclude that the diagnosed apparatus operates abnormally, and a predetermined value equal to or larger than 1 is set to N.

If the counter value is equal to or less than N (i.e., the range of the counter value is 1 to N) (NO in S209), it is determined that the subject data is the malfunction data candidate for the second time to N+1 times in S206 to increment the counter value by 1. The diagnosing apparatus further updates the feature quantity of the malfunction data candidate using the feature quantity of the input data, and stores that data in the memory. With this configuration, even in case that the feature quantity that reflects a malfunction changes as a condition of the apparatus gradually changes while the diagnosed apparatus is repeatedly performing the operating sequence, the diagnosing apparatus can correctly determine whether or not the diagnosed apparatus operates normally or abnormally.

If the counter value is larger than N (YES in S209), the operation proceeds to S210 to determine that the diagnosed apparatus operates abnormally, and the operation ends.

In this embodiment, as described above, in S209, the feature quantity of the malfunction data candidate is updated (replaced) using the feature quantity of the input data. However, by using the feature quantity of the previous malfunction data candidate that has been already stored, it is possible to calculate average values for each frequency and updates the feature quantity of the malfunction data candidate using the calculated result.

Embodiment 3

Next, in this embodiment, in accordance with a type of the operating sequence determined as reflecting a malfunction, the number of times of repeating the operating sequence N (i.e., N is equal to or larger than 1) determined as reflecting a malfunction is modified to determine whether or not the diagnosed apparatus operates abnormally.

In the second embodiment, the number of times of repeating the operating sequence N repeated if the malfunction candidate is determined is modifiable. That is, the following embodiment is substantially the same as the second embodiment described above, except that the number of repetition times N is modified in accordance with the operating sequence that the malfunction candidate is determined.

Figure 8:
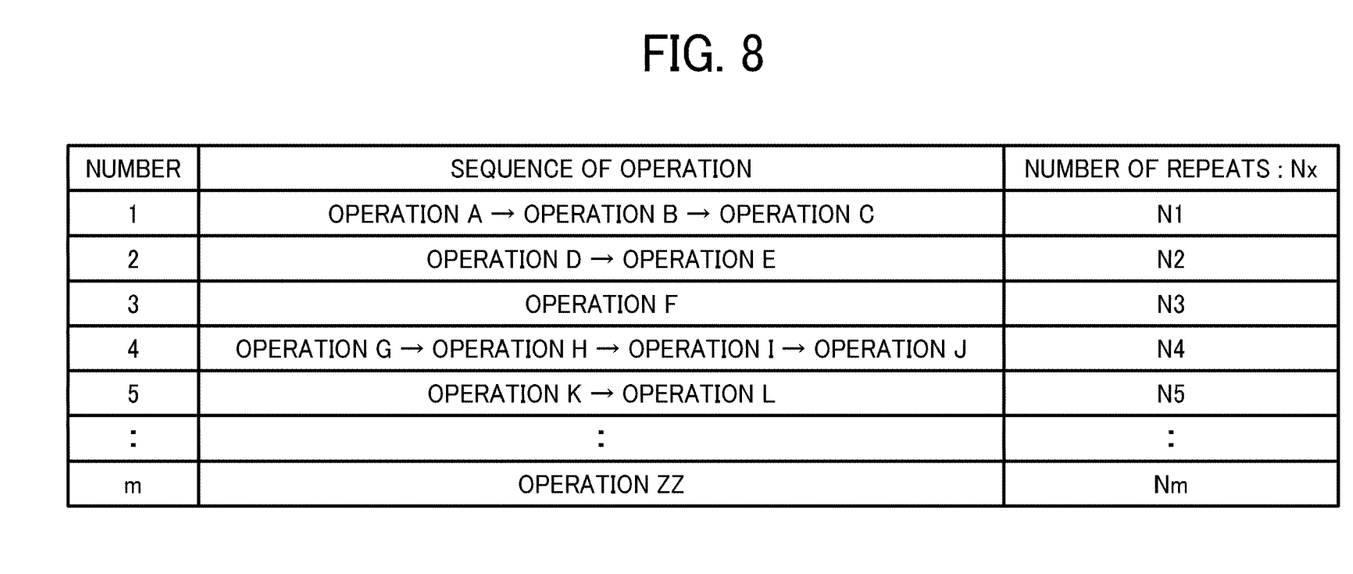
FIG. 8 is a table illustrating association between operating sequence and the number of repetition times N.

FIG. 8 is a table illustrating association between operation sequence and the number of repetition times N, which is stored in, for example, the ROM 12.

Identification numbers 1 to m are assigned to operating sequences respectively, and the number of repetition times Nx (i.e., the number of times itself is modifiable) is defined for each operating sequence.

In this case, as illustrated in FIG. 8, numbers 1 to m are assigned to operating sequences to be performed by the diagnosed apparatus. The number of repetition times N1 is previously set for the operating sequence assigned with the number 1, that subsequently performs operation A, operation B, and operation C. The number of repetition times N2 is previously set for the operating sequence assigned with the number 2, that subsequently performs operation D and operation E. The number of repetition times N3 is previously set for the operating sequence assigned with the number 3, that performs operation F. The number of repetition times N4 is previously set for the operating sequence assigned with the number 4, that subsequently performs operation G, operation H, operation I, and operation J. The number of repetition times N5 is previously set for the operating sequence assigned with the number 5, that subsequently performs operation K and operation L. The number of repetition times Nm is previously set for the operating sequence assigned with the number m, that performs operation ZZ.

The number of repetition times Nx is an integer value that defines the number of times that the diagnosing apparatus determines as the diagnosed apparatus has the malfunction data candidate, before concluding that the diagnosed apparatus operates abnormally. The number of repetition times Nx is set for each operating sequence. For example, a value equal to or larger than 1 may be set as the number of repetition times Nx.

Figure 9:
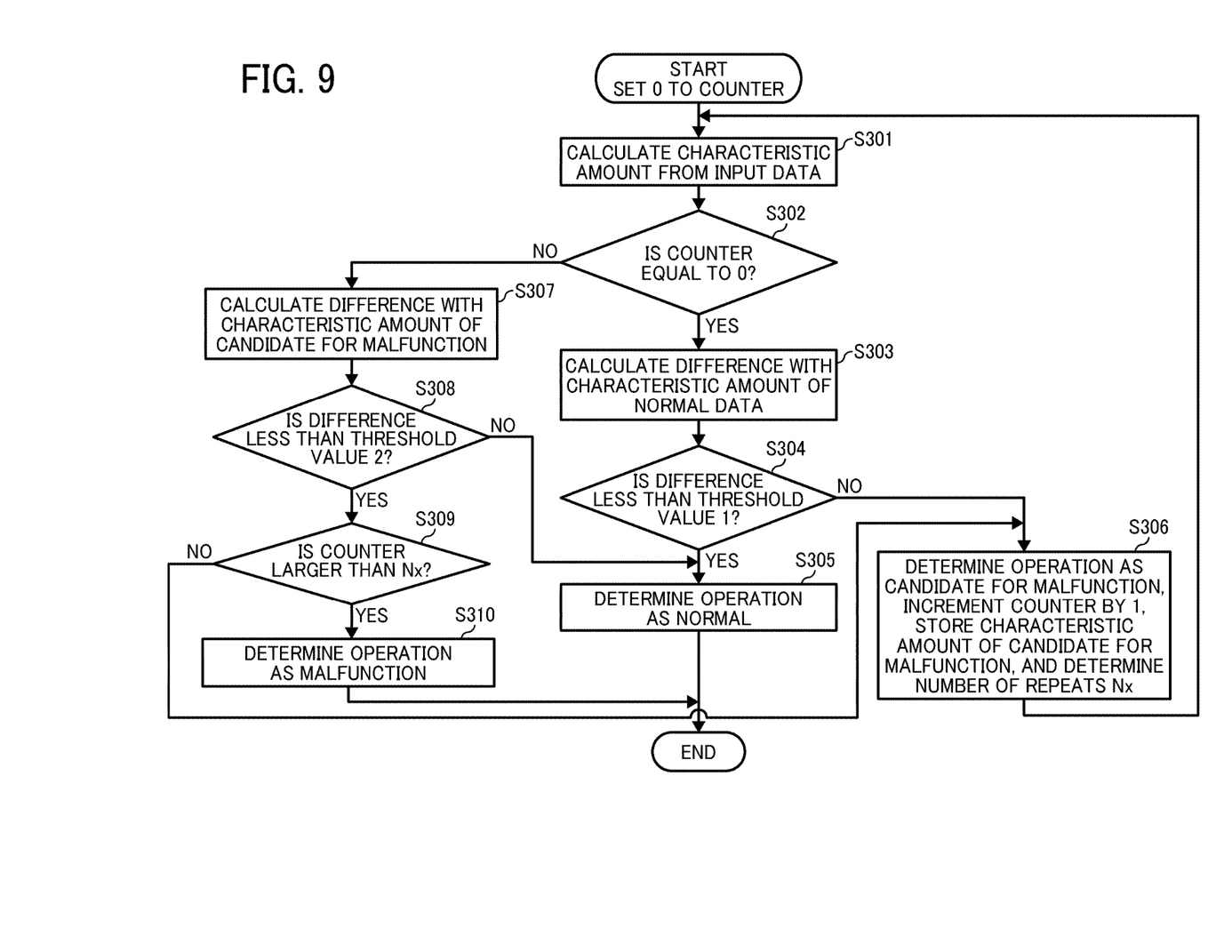
FIG. 9 is a flowchart illustrating an operation of determining malfunction as an embodiment of the present invention.

FIG. 9 is a flowchart illustrating an operation of determining malfunction in this embodiment.

The operation of FIG. 9 is substantially similar to the operation of FIG. 7, except for replacement of S206 with S306. That is, S301 to 310 are performed in a substantially similar manner as described above referring to S201 to S210, except for S306. Therefore, only step S306 is described below with reference to the above descriptions in the first embodiment and the second embodiment.

In S306, if the input data is determined as the malfunction data candidate, based on the association table in FIG. 8, the diagnosing apparatus 1 reads the number of repetition times Nx from the ROM 12, and uses that read data to be compared with the counter value used in S309.

Since the number of repetition times is modifiable for each operation, it is possible to increase the number of times of repeating an operation that may easily cause an error in determination, compared to the number of times of repeating other operations. This further enhances precision in determining whether or not the diagnosed apparatus operates abnormally.

In another example, if a malfunction that may damage the diagnosed apparatus itself can be presumed through performing a specific operating sequence, to minimize damage to the diagnosed apparatus, the number of repetition times for such operating sequence is set to 1. For example, in consideration of occurring timings of abnormal sound, loudness of the abnormal sound, and frequency of the abnormal sound, it is presumed that a driving shaft is broken and it is possible to have an impact on other surrounding parts by operating the apparatus. In such case, the operating sequence is not repeated.

By contrast, if it is presumed that it is not most likely to have a large impact on the diagnosed apparatus itself even in case the operating sequence is performed repeatedly, it is presumed that the diagnosed apparatus would not be damaged even in case of repeating the operating sequence. Accordingly, in order to further enhance precision of determining whether or not the diagnosed apparatus operates abnormally, the number of repetition times is increased. Examples of such case include a case in which a driving gear is worn away and slight abnormal sound occurs.

In the above description, in S108, S208, and S308, the difference between the feature quantity of the input data and the feature quantity of the malfunction data candidate is calculated for each frequency. After comparing the calculated differences with the predetermined threshold value 2 for each frequency, if the calculated difference is equal to or larger than the threshold value 2, it is determined that the apparatus operates normally. However, it is possible to reset the counter value to 0 and perform the operation again from S101, S201, and S301.

Embodiment 4

In this embodiment, if it is determined that the diagnosed apparatus operates abnormally for the first time, the operating sequence indicating such malfunction is repeated. If it is determined that the diagnosed apparatus operates abnormally for multiple times, an alert level is modified and an alert is displayed on the alert display (display unit).

That is, in any one of the embodiments 1 to 3, in case of determining the malfunction data candidate, if it is determined that the diagnosed apparatus operates abnormally for the number of times more than the number of repetition times N for the repeated operating sequence, it concludes that the apparatus operates abnormally. However, in this embodiment, if it is determined the input data as malfunction candidate data for the number of times equal to or less than the number of repetition times N and it concludes that the apparatus operates normally, an alert is displayed on the output unit. Here, an operation of displaying the alert is described below.

Figure 10:
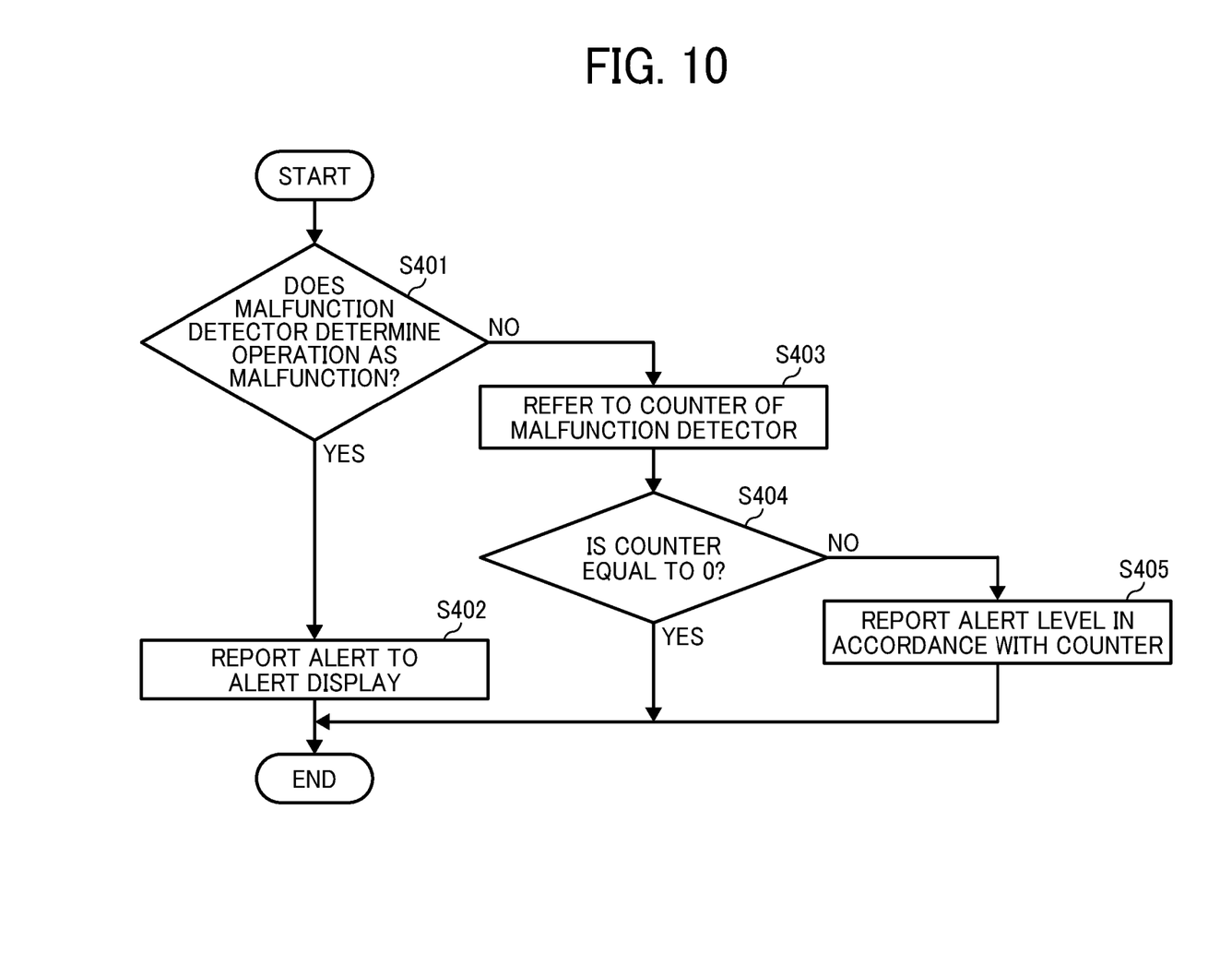
FIG. 10 is a flowchart illustrating an operation of reporting an alert to an output display unit based on the number of times that a malfunction detector determines as a candidate for malfunction data.

FIG. 10 is a flowchart illustrating an operation of reporting an alert with an output unit 104 to an output display unit based on the number of times that a malfunction detector 103 determines input data as a candidate for malfunction.

First, the output unit 104 determines whether or not the diagnosed apparatus operates abnormally based on the determination result by the malfunction detector 103 in S401. If it is determined that the diagnosed apparatus operates abnormally with the determination result (YES in S401), an alert indicating that malfunction is displayed on the alert display in S402, and the operation ends.

If the determination result indicates that the diagnosed apparatus operates normal (NO in S401), with reference to the counter value of the malfunction detector 103 in S403, it is determined whether or not the counter value is 0 in S404. If the counter value is equal to 0 (YES in S404), the operation ends as is.

If the counter value is not equal to 0 (NO in S404), an alert level is determined in accordance with the counter value. After reporting the determined alert level to the alert display in S405, the operation ends.

In S405, it is possible to report that information not only to the alert display but also to the service center.

A level value 1 to 3 is set to the alert level in accordance with the counter value.

In the malfunction detector 103, regardless of whether or not the operating sequence indicates normal, the counter value is hold for a predetermined period of time.

Figure 11:
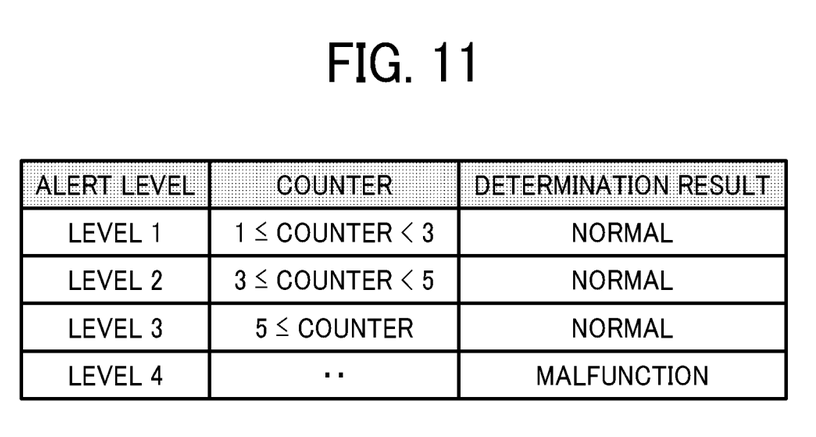
FIG. 11 is a table illustrating a relationship among an alert level, a counter value, and a determination result by the malfunction detector.

FIG. 11 is a table illustrating a relationship among an alert level, a counter value, and a determination result by the malfunction detector.

In this case, the alert levels are respectively set to level 1 to 4 in accordance with the counter value, and in level 4, the determination result indicates that the apparatus operates abnormally.

That is, if it is determined that the apparatus operates normally and the counter value is equal to or larger than 1, the malfunction detector 103 determines the alert level in accordance with the table in FIG. 9.

That is, in this case, if the counter value is equal to or larger than 1 and less than 3, the alert level is set to level 1. If the counter value is equal to or larger than 3 and less than 5, the alert level is set to level 2. If the counter value is equal to or larger than 5, the alert level is set to level 3. If the determination result is level 1 to level 3, it is determined that the apparatus operates normally. If the determination result is level 4, it is determined that the apparatus operates normally.

In the alert display, different information is displayed on the display in accordance with the reported level. For example, that information is displayed in different color for each level. By displaying the information in different ways, it is possible to report to the user detailed information. In one example, the report indicates that the input data that is determined as malfunction data candidate occurred once but a conclusion is made that the apparatus operates normally. In another example, the report indicates how many times the input data has been determined as a malfunction data candidate.

In the above-described example embodiment, a computer can be used with a computer-readable program, described by object-oriented programming languages such as C++, Java (registered trademark), JavaScript (registered trademark), Perl, Ruby, or legacy programming languages such as machine language, assembler language to control functional units used for the apparatus or system. For example, a particular computer (e.g., personal computer, workstation)

may control an information processing apparatus or an image processing apparatus such as image forming apparatus using a computer-readable program, which can execute the above-described processes or steps. In the above-described embodiments, at least one or more of the units of apparatus can be implemented as hardware or as a combination of hardware/software combination. The computer software can be provided to the programmable device using any storage medium or carrier medium for storing processor-readable code such as a floppy disk, a compact disk read only memory (CD-ROM), a digital versatile disk read only memory (DVD-ROM), DVD recording only/rewritable (DVD-R/RW), electrically erasable and programmable read only memory (EEPROM), erasable programmable read only memory (EPROM), a memory card or stick such as USB memory, a memory chip, a mini disk (MD), a magneto optical disc (MO), magnetic tape, a hard disk in a server, a solid state memory device or the like, but not limited these.

Numerous additional modifications and variations are possible in light of the above teachings. It is therefore to be understood that within the scope of the appended claims, the disclosure of the present invention may be practiced otherwise than as specifically described herein.

For example, elements and/or features of different illustrative embodiments may be combined with each other and/or substituted for each other within the scope of this disclosure and appended claims.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

The invention claimed is:

1. A malfunction diagnosing apparatus comprising:
   memory storing computer-readable instructions; and
   one or more processors configured to execute the computer-readable instructions such that the one or more processors are configured to perform operations including,
   collecting first vibration data generated at a target apparatus when the target apparatus performs a sequence of operations;
   analyzing the collected first vibration data to obtain a feature quantity of the collected first vibration data;
   comparing the obtained feature quantity with a stored feature quantity;
   determining, based on the comparison, whether or not the target apparatus may be operating abnormally;
   based on a determination indicating that the target apparatus may be operating abnormally, instructing the target apparatus to repeat the same sequence of operations for a predetermined number of times to determine if a potential abnormality exists, to additionally collect vibration data, analyzing the additionally collected vibration data, and comparing the first vibration data to the additionally collected vibration data to determine abnormality based on the feature quantity for the predetermined number of times; and
   determining that a malfunction occurs in the target apparatus when the determination indicates that the target apparatus operates abnormally for the predetermined number of times.

2. The malfunction diagnosing apparatus according to claim 1,
   wherein the predetermined number of times for repeating the sequence of operations is modifiable.

3. The malfunction diagnosing apparatus according to claim 1, wherein the one or more processors are further configured
   to output an alert based on a determination result indicating that the malfunction occurs in the target apparatus, and
   change a level of the alert stepwise in accordance with the number of times of repeating the operating sequence indicating abnormality of the target apparatus.

4. The malfunction diagnosing apparatus according to claim 1, wherein the one or more processors are further configured to
   set the number of repetition times for the sequence of operations to 1 when it is determined that a malfunction may damage the target apparatus through performing the sequence of operations based on at least one of timings of an abnormal sound, loudness of an abnormal sound, and frequency of an abnormal sound.

5. The malfunction diagnosing apparatus according to claim 2,
   wherein, in case of determining abnormality of the target apparatus for the sequence of operations subsequent to the first sequence of operation that has been firstly performed, the one or more processors are further configured to
   determine the feature quantity obtained for the first sequence and indicate abnormality of the target apparatus, as a feature quantity of reference malfunction data,
   obtain a difference between the feature quantity of the reference malfunction data and a feature quantity that reflects vibration data collected in performing the operating sequence subsequent to the first sequence of operation, and
   determine whether or not a malfunction occurs in the target apparatus based on a comparison between the obtained difference in feature quantity and a threshold.

6. The malfunction diagnosing apparatus according to claim 2,
   wherein the number of times of repeating the sequence of operations is modifiable for each of the first sequence of operations that has been firstly performed and indicated that the target apparatus operates abnormally.

7. The malfunction diagnosing apparatus according to claim 3, wherein when the determination result indicates abnormality, the one or more processors are further configured to send the alert e-mail to a service center in charge of maintenance of the target apparatus via the Internet.

8. A method of diagnosing malfunction performed by a malfunction diagnosing apparatus, the method comprising:
   collecting vibration data generated when a diagnosed apparatus operates in an operating sequence and storing the collected vibration data in a memory;
   analyzing, via one or more processors, the collected vibration data and calculate a feature quantity by comparing the calculated feature quantity with a stored feature quantity;
   determining, via the one or more processors, based on the comparison, whether or not something is wrong with the diagnosed apparatus;
   controlling, via the one or more processors, when it is determined that something may be wrong with the diagnosed apparatus, the diagnosed apparatus to repeat the same operating sequence a predetermined number of times to determine if a potential abnormality exists; and determining that a malfunction occurs in the diagnosed apparatus when it is determined that something is wrong with the diagnosed apparatus in the operating sequence repeated for the predetermined number of times.

9. The method of diagnosing malfunction according to claim 8, the method further comprising:

enabling to modify, in case of repeating the operating sequence that it is determined that something is wrong with the diagnosed apparatus for the predetermined number of times, the number of times of repeating the operating sequence subsequent to a first repetition.

10. The method of diagnosing malfunction according to claim 8, the method further comprising:

outputting an alert based on a determination result indicating that the malfunction occurs in the diagnosing target apparatus; and changing a level of the alert stepwise in accordance with the number of times of repeating the operating sequence indicating abnormality of the diagnosing target apparatus.

11. The method of diagnosing malfunction according to claim 9, the method further comprising:

determining, in case of determining abnormality of the diagnosing target apparatus for the sequence of operations subsequent to the first sequence of operation that has been firstly performed, the feature quantity obtained for the first sequence and indicating abnormality of the diagnosing target apparatus, as a feature quantity of reference malfunction data;

obtaining a difference between the feature quantity of the reference malfunction data and a feature quantity that reflects vibration data collected in performing the operating sequence subsequent to the first sequence of operation; and determining whether or not a malfunction occurs in the diagnosing target apparatus based on a comparison between the obtained difference in feature quantity and a threshold.

12. The method of diagnosing malfunction according to claim 9, the method further comprising:

enabling to modify the number of times of repeating the sequence of operations for each of the first sequence of operations that has been firstly performed and indicated that the diagnosing target apparatus operates abnormally.

13. A non-transitory, computer-readable recording medium storing a program that, when executed by one or more processors of a malfunction diagnosing apparatus, causes the processors to implement a method of diagnosing malfunction, comprising:

collecting vibration data generated when a diagnosed apparatus operates in an operating sequence;

analyzing the collected vibration data and calculate a feature quantity;

comparing the calculated feature quantity with a stored feature quantity;

determining, based on the calculated feature quantity, whether or not something is wrong with the diagnosed apparatus;

controlling, if it is determined that something wrong with the diagnosed apparatus, the diagnosed apparatus to repeat the operating sequence that it is determined that something is wrong with the diagnosed apparatus for a predetermined number of times; and determining that malfunction occurs in the diagnosed apparatus if it is determined that something is wrong with the diagnosed apparatus in the operating sequence repeated for the predetermined number of times.

\* \* \* \* \*